United States Patent
Manus et al.

(10) Patent No.: US 11,058,622 B2
(45) Date of Patent: Jul. 13, 2021

(54) METHODS OF TREATING GASTRIC DISORDERS

(71) Applicant: Colgate-Palmolive Company, New York, NY (US)

(72) Inventors: Lisa Manus, Lawrenceville, NJ (US); Michael Stranick, Bridgewater, NJ (US); Donghui Wu, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/714,863

(22) Filed: Dec. 16, 2019

(65) Prior Publication Data

US 2020/0197279 A1 Jun. 25, 2020

Related U.S. Application Data

(60) Provisional application No. 62/782,805, filed on Dec. 20, 2018.

(51) Int. Cl.
*A61K 8/44* (2006.01)
*A61K 8/27* (2006.01)
*A61K 8/362* (2006.01)
*A61Q 11/00* (2006.01)

(52) U.S. Cl.
CPC .......... *A61K 8/44* (2013.01); *A61K 8/27* (2013.01); *A61K 8/362* (2013.01); *A61Q 11/00* (2013.01)

(58) Field of Classification Search
CPC ............ A61K 8/27; A61K 8/44; A61Q 11/00
See application file for complete search history.

(56) References Cited

U.S. PATENT DOCUMENTS

| 7,803,817 B2 | 9/2010 | Kostadinov et al. |
| 9,585,827 B2 | 3/2017 | Stephenson |
| 9,757,316 B2 | 9/2017 | Pan et al. |
| 9,763,865 B2 | 9/2017 | Pan et al. |
| 9,913,784 B2 | 3/2018 | Szewczyk et al. |
| 9,925,130 B2 | 3/2018 | Pan |
| 9,943,473 B2 | 4/2018 | Pan |
| 9,980,890 B2 | 5/2018 | Pan |
| 10,105,303 B2 | 10/2018 | Pan et al. |
| 10,130,571 B2 | 11/2018 | Szewczyk et al. |
| 10,195,125 B2 | 2/2019 | Pan et al. |
| 10,245,222 B2 | 4/2019 | Pan et al. |
| 2017/0209489 A1 | 7/2017 | Geibel |
| 2017/0224595 A1 | 8/2017 | Xu et al. |
| 2018/0243193 A1 | 8/2018 | Pan |
| 2019/0015310 A1 | 1/2019 | Pan |

FOREIGN PATENT DOCUMENTS

| WO | WO-2007089511 A2 * | 8/2007 | ............ A61P 43/00 |
| WO | WO-2014098824 A1 * | 6/2014 | ............ A61K 8/20 |

OTHER PUBLICATIONS

Baig et al., 2014, "Protective effects of SnF2—Part I. Mineral solubilization studies on powdered apatite," Int. Dental Journal 64(Suppl. 1):4-10.

Mohammed et al., 2014, "Physical chemical effects of zinc on in vivo enamel demineralization," Journal of Dentistry 42:1096-1104.

Mohammed et al., 2015, "Inhibitory effects of zinc ions on enamel demineralization kinetics in vitro," Caries Research 49(6):600-605.

Phan et al., 2015, "Gastric hypersecretory states: Investigation and management," Current Treatment Options Gastroenterology 13(4):386-397.

International Search Report and the Written Opinion of the International Searching Authority issued in International Application PCT/US2019/066437 dated Mar. 24, 2020.

* cited by examiner

*Primary Examiner* — Michael P Cohen

(57) ABSTRACT

Provided herein are methods of treating one or more symptoms of a gastric disorder in the oral cavity of a subject in need thereof, wherein the method comprises applying to the subject's teeth an oral care composition comprising a basic amino acid in free or salt form, wherein the basic amino acid is arginine (e.g., free form arginine); zinc oxide and zinc citrate; and an orally acceptable carrier.

8 Claims, No Drawings

METHODS OF TREATING GASTRIC DISORDERS

CROSS REFERENCE TO RELATED APPLICATIONS

This application claims priority to U.S. Provisional Application No. 62/782,805, filed on Dec. 20, 2019, the contents of which are incorporated herein by reference in its entirety.

FIELD

This invention relates to methods of treating symptoms pertaining to gastric disorders, comprising the application of oral care compositions comprising a zinc-amino acid complex, e.g., a zinc-lysine-chloride complex, e.g., ZLC, and an orally acceptable carrier, to a subject's tooth; as well as to methods of using, methods of identification of novel candidate compounds, compounds for use, and of making these compositions.

BACKGROUND

Dental enamel is a thin, hard layer of calcified material that covers the crown of teeth. The major mineral component of dental enamel is hydroxyapatite, a crystalline form of calcium phosphate. Chemical erosion of dental enamel may arise from tooth exposure to acidic food and drinks (extrinsic) or to stomach acids (intrinsic) arising from gastric reflux. The erosion of dental enamel can lead to enhanced tooth sensitivity due to increased exposure of the dentin tubules and increased dentin visibility leading to the appearance of more yellow teeth. The salivary pellicle (a thin layer of salivary glycoproteins deposited on teeth) is integral in protecting the teeth against an erosive challenge. As a result, people that experience xerostomia are more susceptible to acid erosion damage.

The sustained presence of intrinsic acid in the oral cavity can be damaging to the enamel of the tooth. In some cases, regurgitation of stomach acids following meals, especially after overeating, can be considered normal, for up to about 1 hour a day. However, for people with certain gastric disorders, such as gastroesophageal reflux disease (GERD), the intrusion of gastric acids into the oral cavity during, for example sleep, is especially damaging to the teeth, as salivation and swallowing are reduced, and, in a supine position, the lower molars can be bathed in the acids.

Zinc is a well-known antimicrobial agent used in toothpaste compositions. Zinc is also a well-known essential mineral for human health, and has been reported to help strengthen dental enamel and to promote cell repair. However, formulations with zinc have a variety of challenges. Unfortunately, conventional toothpaste formulations often require a high concentrations of zinc, e.g., 2% by weight or more, to achieve efficacy. And, at this concentration, the zinc imparts a notably astringent taste to the composition.

Consequently, there is still the need to provide improved methods of using oral care compositions to protect tooth enamel from the effects of intrinsic stomach acid erosion.

BRIEF SUMMARY

The present inventors have unexpectedly found that combinations of a basic amino acid (i.e., arginine) and one or more sources of zinc (i.e., zinc oxide and zinc citrate, e.g., zinc citrate trihydrate), are effective in inhibiting or decreasing calcium release in tooth enamel exposed to acid. Without being bound by theory, it is believed that these compositions have beneficial effects in inhibiting, repairing, or mitigating the effects of dental erosion.

In the Examples listed herein, the inventors have detailed how toothpaste slurries with the combination a zinc-amino acid complex, e.g., a zinc-lysine-chloride complex, e.g., ZLC are effective in inhibiting or limiting the amount calcium that is released from Calcium-deficient HA powder upon exposure to citric acid. As noted below, Calcium-deficient HA is chosen to mimic calcium-phosphate material given its similarity in structure, and elemental composition, to dental enamel. Citric acid is also an excellent chelating agent, binding metals by making them soluble. Not being bound by any particular theory, but given citric acid's ability to act as a potent chelator, the ability of the Test Formulation toothpaste slurries described in the Examples—containing a zinc-amino acid complex, e.g., a zinc-lysine-chloride complex, e.g., ZLC—to limit or inhibit calcium release is all the more impressive.

Without being bound by theory, the ability to limit or inhibit calcium release, under such acid conditions described herein, demonstrates how the methods described herein can be effective in treating symptoms (e.g., tooth enamel loss) that occur when gastric disorders (e.g., GERD, heartburn, indigestion) result in the elevation (or prolonged presence) of gastric acid in the oral cavity.

Accordingly, in one aspect, the present invention relates to a method (Method 1.0) of treating one or more symptoms of a gastric disorder in the oral cavity of a subject in need thereof, wherein the method comprises applying to the subject's teeth an oral care composition comprising:
  a.) a zinc-amino acid complex, e.g., a zinc-lysine-chloride complex, e.g., ZLC;
  b.) and an orally acceptable carrier.
For example, Method 1 comprises:
  1.1 Method 1.0, wherein the one or more symptoms the gastric disorder is dental erosion (e.g., tooth enamel erosion) that is consequent to the presence of gastric acid (e.g., stomach acid) in the oral cavity (e.g., increased or elevated amounts of gastric acid).
  1.2 Method 1.1, wherein the dental erosion (e.g., erosion of the tooth enamel) that is consequent to the presence of gastric acid refers to the erosion of the subject's tooth enamel from loss of calcium.
  1.3 Any of the preceding methods, wherein the oral care composition inhibits or decreases the release of calcium from the subject's tooth enamel.
  1.4 Any of the preceding methods, wherein the in the inhibition or decrease of the release of calcium in the subject's tooth enamel is relative to a reference standard.
  1.5 Any of the preceding methods, wherein the oral care composition inhibits the release of calcium relative to one or more oral care compositions that do not contain zinc.
  1.6 Any of the preceding methods, wherein the gastric disorder increases the amount of gastric acid in the oral cavity (e.g., relative to a reference standard).
  1.7 Any of the preceding methods, wherein the gastric disorder prolongs the period which gastric acid is present in a subject's oral cavity (e.g., relative to a reference standard).
  1.8 Any of the preceding methods, wherein the subject has a gastric disorder that increases the amount of gastric acid in the oral cavity of the subject (and/or prolongs the oral cavity to exposure of gastric acid), and wherein the gastric disorder is selected from the group consisting of: duodenal ulcers, gastric ulcers, gastroesophageal reflux disease (GERD), erosive esophagitis, gastroesophageal reflux disease weakly reactive (poorly responsive symptomatic gastroesophageal reflux disease), bulimia nervosa, pathological gastrointestinal hypersecretory disease (pathological gastrointestinal hypersecretory disease), Zhuo-Ellison syndrome, heartburn, and acid indigestion.

1.9 Method of 1.7, wherein the gastric disorder is gastroesophageal reflux disease (GERD).

1.10 Any of the preceding methods, wherein the one or more symptoms is that the subject is exposed to gastric acids in the oral cavity during sleep.

1.11 Any of the preceding methods, wherein the subject is at risk for dental erosion.

1.12 Method of 1.10, wherein the risk for dental erosion is selected from the group consisting of xerostomia, hypersensitivity, weakened tooth integrity (e.g., from one or more tooth fractures), and where the subject has tooth discoloration.

1.13 Any of the preceding methods, wherein the amount of gastric acid in the oral cavity is elevated relative to a reference standard.

1.14 Any of the preceding methods, wherein the amino acid is selected from lysine, glycine and arginine, in free or orally acceptable acid addition salt form, e.g., hydrochloride form.

1.15 Any of the preceding methods, wherein the amino acid is a basic amino acid, e.g., arginine or lysine, in free or orally acceptable salt form.

1.16 Any of the preceding methods, wherein the oral care composition comprises a halide in ionic association with the zinc and amino acid.

1.17 Any of the preceding methods, wherein the molar ratio of Zn:amino acid is from 3:1 to 1:5, e.g., about 1:2 and the molar ratio of Zn:halide where present is from 3:1 to 1:3, e.g., about 1:2. 1.18 Any of the preceding methods, wherein the zinc-amino acid complex is formed, in whole or in part, in situ after the composition is applied.

1.19 Any of the preceding methods, wherein the zinc-amino acid complex is formed, in whole or in part, in situ after the composition is formulated.

1.20 Any of the preceding methods, wherein the amino acid is lysine.

1.21 Any of the preceding methods, wherein zinc is present in an amount of 0.05 to 10% by weight of the composition, optionally at least 0.1, at least 0.2, at least 0.3, at least 0.4, at least 0.5, at least 1, at least 2, at least 3, or at least 4 up to 10% by weight of the composition, e.g. about 1-3%, e.g., about 2-2.7% by weight.

1.22 Any of the preceding methods, wherein amino acid is present in an amount of 0.05 to 30% by weight of the composition, optionally at least 0.1, at least 0.2, at least 0.3, at least 0.4, at least 0.5, at least 1, at least 2, at least 3, at least 4, at least 5, at least 10, at least 15, at least 20 up to 30% by weight, e.g., about 1-10% by weight.

1.23 Any of the preceding methods, wherein a molar ratio of zinc to amino acid is 2:1 to 1:4, optionally 1:1 to 1:4, 1:2 to 1:4, 1:3 to 1:4, 2:1 to 1:3, 2:1 to 1:2, or 2:1 to 1:1, e.g., about 1:2 or 1:3. 1.24 Any of the preceding methods, wherein the oral care composition comprises a halide in ionic association with the zinc and amino acid, wherein the halide is selected from the group consisting of fluorine, chlorine, and mixtures thereof 1.25 Any of the preceding methods, wherein the zinc amino acid complex is a zinc lysine chloride complex (e.g., $(ZnLys_2Cl)^+Cl^-$ or $(ZnLys_3)^{2+}Cl_2$) or a zinc arginine chloride complex.

1.26 Any of the preceding methods, wherein the zinc amino acid complex is a zinc lysine chloride complex, e.g., ZLC, e.g., a zinc lysine chloride complex having the chemical structure $[Zn(C_6H_{14}N_2O_2)_2Cl]^+Cl^-$, either in solution of the cationic complex (e.g., $[Zn(C_6H_{14}N_2O_2)_2Cl]^+$) and the chloride anion, or in solid salt form, e.g., crystal form, optionally in mono- or dihydrate form.

1.27 Any of the preceding methods, wherein the oral care composition is in the form of a clear gel which provides a zinc oxide precipitate when diluted.

1.28 Any of the preceding methods, wherein the oral care composition is in the form of a dentifrice, e.g., wherein the zinc-amino acid complex is present in an effective amount, e.g., in an amount of 0.5-4% by weight of zinc, e.g., about 1-3% by weight of zinc, in a dentifrice base.

1.29 Any of the preceding methods, wherein the oral care composition is in the form of a dentifrice, wherein the dentifrice base comprises an abrasive, e.g., an effective amount of a silica, e.g., 10-30%, e.g., about 20%.

1.30 Any of the preceding methods, wherein the zinc-amino acid complex is present in an effective amount, e.g., in an amount of 0.1-3% by weight of zinc, e.g., about 0.2-1% by weight of zinc.

1.31 Any of the preceding methods, wherein the zinc-amino acid complex is ZLC.

1.32 Any of the preceding methods, wherein the zinc-amino acid complex is ZLC and is present in an amount of 2-6% of the composition by weight.

1.33 Any of the preceding methods, wherein the oral composition further comprises "soluble phosphate salts", and wherein soluble phosphate salts include an orally acceptable phosphate salt having a solubility in water of at least 1 g/100 ml at 25° C.

1.34 Any of the preceding methods, wherein the one or more soluble phosphate salts are sodium and/or potassium salts of pyrophosphates and/or polyphosphates, e.g., tripolyphosphates.

1.35 Any of the preceding methods, wherein the one or more soluble phosphate salts comprise tetrasodium pyrophosphate (TSPP), sodium tripolyphosphate (STPP), tetrapotassium pyrophosphate (TKPP), or combinations thereof.

1.36 Any of the preceding methods, wherein the one or more soluble phosphate salts are present in an amount of 1-20%, e.g., 2-8%, e.g., ca. 5%, by weight of the composition.

1.37 Any of the preceding methods, wherein the oral care composition further comprises an effective amount of a fluoride ion source, e.g., providing 500 to 3000 ppm fluoride.

1.38 Any of the preceding methods, wherein the oral care composition comprises an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.39 Any of the preceding methods, wherein the oral care composition wherein the dentifrice base comprises a humectant, e.g., selected from glycerin, sorbitol, propylene glycol, polyethylene glycol, xylitol, and mixtures thereof, e.g. comprising at least 30%, e.g., 40-50% glycerin, by weight of the composition.

1.40 Any of the preceding methods, wherein the oral care composition comprises one or more surfactants, e.g., selected from anionic, cationic, zwitterionic, and non-ionic surfactants, and mixtures thereof.

1.41 Any of the preceding methods, wherein the dentifrice base comprises an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS) by weight of the composition.

1.42 Any of the preceding methods, wherein the dentifrice base comprises a zwitterionic surfactant, for example a betaine surfactant, for example cocamidopropylbetaine, e.g. in an amount of from about 0.1% to about 4.5% by weight, e.g. 0.5-2% cocamidopropylbetaine by weight of the composition 1.43 Any of the preceding methods, wherein the oral care composition comprises a dentifrice base.

1.44 Any of the preceding methods, wherein the oral care composition comprises a viscosity modifying amount of one or more of polysaccharide gums, for example xanthan gum or carrageenan, silica thickener, and combinations thereof.

1.45 Any of the preceding methods, wherein the oral care composition comprises gum strips or fragments.

1.46 Any of the preceding methods, wherein the oral care composition comprises flavoring, fragrance and/or coloring.

1.47 Any of the preceding methods, wherein the oral care composition comprises an effective amount of one or more antibacterial agents in addition to the zinc-amino acid complex, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.

1.48 Any of the preceding methods, wherein the oral care composition comprises an antibacterially effective amount of triclosan, e.g. 0.1-0.5%, e.g. about 0.3% by weight of the composition.

1.49 Any of the preceding methods, wherein the oral care composition comprises a whitening agent, e.g., a selected from the group consisting of peroxides, metal chlorites, perborates, percarbonates, peroxyacids, hypochlorites, and combinations thereof.

1.50 Any of the preceding methods, wherein the oral care composition comprises hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.51 Any of the preceding methods, wherein the oral care composition comprises an agent that interferes with or prevents bacterial attachment, e.g., solbrol or chitosan.

1.52 Any of the preceding methods, wherein the oral care composition comprises a soluble calcium salt, e.g., selected from calcium sulfate, calcium chloride, calcium nitrate, calcium acetate, calcium lactate, and combinations thereof.

1.53 Any of the preceding methods, wherein the oral care composition comprises a physiologically or orally acceptable potassium salt, e.g., potassium nitrate or potassium chloride, in an amount effective to reduce dentinal sensitivity.

1.54 Any of the preceding methods, wherein the oral care composition comprises an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.

1.55 Any of the preceding methods, wherein the oral care composition comprises a breath freshener, fragrance or flavoring.

1.56 Any of the preceding methods, wherein the pH of the oral care composition is approximately neutral, e.g., about pH 7.

1.57 Any of the preceding methods, wherein the oral care composition comprises the zinc-amino acid complex is ZLC in an amount of 2-6% by weight of the composition; and an orally acceptable carrier.

1.58 Any of the preceding methods, wherein the oral care composition comprises
  a.) the zinc-amino acid complex is ZLC in an amount of 2-6% by weight of the composition; and
  b.) one or more soluble phosphate salts are selected from tetrasodium pyrophosphate (TSPP), sodium tripolyphosphate (STPP), tetrapotassium pyrophosphate (TKPP), and
  c.) combinations thereof in an amount of 2-6% by weight of the composition; and
  d.) a dentifrice base comprises
    an effective amount of a fluoride ion source,
    silicas,
    humectant,
    thickener,
    anionic surfactant, e.g., sodium lauryl sulfate,
    zwitterionic surfactant, e.g., cocamidopropyl betaine
    flavoring and sweetener.

1.59 Any of the preceding methods, wherein the oral care composition may be any of the following oral compositions selected from the group consisting of: a toothpaste or a dentifrice, a mouthwash or a mouth rinse, a topical oral gel, and a denture cleanser.

1.60 Any of the preceding methods, wherein the oral care composition is in the form of a chewing gum.

1.61 Any of the preceding methods, where the oral care composition is further used to in an effective amount to clean the teeth, reduce bacterially-generated biofilm and plaque, reduce gingivitis, inhibit tooth decay and formation of cavities, and reduce dentinal hypersensitivity.

A composition obtained or obtainable by combining the ingredients as set forth in any of Method 1, et seq.

A composition for use as set forth in any of Method 1, et seq.

In another embodiment, the invention relates to a method to identify candidate oral care composition that are useful to treat one or more symptoms of a gastric disorder in the oral cavity of a subject in need thereof. (Method 2)

Therefore, Method 2 includes 2.1, which is a method to identify candidate oral care composition that are useful to treat one or more symptoms of a gastric disorder in the oral cavity of a subject in need thereof, wherein Method 2.1 comprises the steps of providing a first sample and a second sample, e.g., toothpaste slurries, wherein the first and second samples have the same initial calcium concentrations; contacting the first sample with a measured quantity of acidic substance, e.g., aqueous acids (i.e., 1% Citric Acid solution (w/w)) to form a solution; contacting the first sample with a candidate oral care composition; determining whether the amount of calcium which is released; contacting the second sample with the measured quantity of acidic substance to form a solution; contacting the second sample with any of the compositions described in Method 1, et seq.; determining whether the calcium released in the second sample solution has changed, wherein the amount of calcium released, in the first sample, being less than or equal to that of the second sample indicates that the candidate oral care composition are useful to treat one or more symptoms of a gastric disorder in the oral cavity of a subject in need thereof.

In one further aspect, Method 2.1 contemplates an embodiment where the first and second samples are added simultaneously with the acidic substance.

In one aspect, the invention contemplates that a candidate oral care composition that is useful to treat one or more symptoms of a gastric disorder in the oral cavity of a subject in need thereof, is identified using the method of Method 2.1.

In one aspect, disclosed is an oral care composition (Composition 1.0) comprising:
  a.) a zinc-amino acid complex, e.g., a zinc-lysine-chloride complex, e.g., ZLC; and
  b.) an orally acceptable carrier.
Wherein the composition inhibits calcium release when measured against a reference standard, as measured when challenged in an acid aqueous solution with citric acid in an amount of about 1% (w/w).

For example, Composition 1.0 can be any of the compositions as described in Method 1.0, et seq.

The invention further relates to a method to treat acid-related conditions in the oral cavity, comprising administering to a subject any of any of the composition described in Method 1.0, et seq.

The disclosure further provides a method of making a dentifrice comprising a zinc amino acid complex and one or more soluble phosphate salts, e.g., any of the compositions described in Method 1.0, et seq., comprising combining a zinc ion source with an amino acid, in free or salt form (e.g., combining zinc oxide with lysine hydrochloride), in an aqueous medium, optionally isolating the complex thus formed in solid salt form, and combining the complex with the soluble phosphate salts in a dentifrice base.

For example, in various embodiments, in addition to the methods of Method 1.0, et seq., the disclosure further comprises additional methods, wherein upon application to the teeth, to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of the compositions described in Method 1.0, et seq. as described above to the oral cavity of a person in need thereof, e.g., one or more times per day. The disclosure further provides the compositions as described in Method 1.0, et seq. for use in any of these methods.

The disclosure further provides the use of soluble phosphate salts, zinc and an amino acid to make an oral care composition comprising phosphate salts and a zinc-amino acid complex as described in any of Method 1.0.

The disclosure further provides the use of a zinc amino acid complex, for example a zinc amino acid halide, for example a zinc-lysine-chloride complex, together with phosphate salts to reduce and inhibit acid erosion of the enamel, clean the teeth, reduce bacterially-generated biofilm and plaque, reduce gingivitis, inhibit tooth decay and formation of cavities, and/or reduce dentinal hypersensitivity.

Without intending to be bound by theory, it is believed that the formation of the zinc amino acid halide, i.e., of the compositions described in Method 1.0, et seq, proceeds via formation of the zinc halide then coordination of amino acid residues around a central zinc. Using reaction of ZnO with lysine hydrochloride in water as an example, the zinc can react with lysine and/or lysine.HCl to form a clear solution of Zn-lysine-chloride complex ($ZnLys_3Cl_2$), wherein $Zn^{++}$ is located in an octahedral center coordinated with two oxygen and two nitrogen atoms in the equatorial plane coming from two lysine's carboxylic acids and amine groups respectively. The zinc is also coordinated to the third lysine via its nitrogen and carboxylic oxygen, at the apical position of the metal geometry.

In another embodiment, the compositions as described in Method 1.0, et seq, can possess a zinc cation is complexes with two amino acid residues and two chloride residues. For example, where the amino acid is lysine, the complex has the formula $[Zn(C_6H_{14}N_2O_2)_2Cl]^+Cl^-$. In this complex, Zn cation is coordinated by two lysine ligands with two N atoms from $NH_2$ groups and O atoms from carboxylic groups in an equatorial plane. It displays a distorted square-pyramidal geometry with the apical position occupied by a $Cl^-$ atom. This novel structure gives rise to a positive cation moiety, to which a $Cl^-$ anion is combined to form an ionic salt.

Other complexes of zinc and amino acid are possible, and the precise form is dependent in part on the molar ratios of the precursor compounds, e.g., if there is limited halide, halide-free complexes may form, e.g. $ZnOLys_2$, having a pyramid geometry, with the equatorial plane that is same as the above compound (Zn is bound to two oxygen and two nitrogen atoms from different lysines), wherein the top of the pyramid is occupied by an O atom.

Mixtures of complexes and/or additional complex structures, e.g., involving multiple zinc ions based on the zinc structure, are possible and contemplated within the scope of the disclosure. When the complexes are in solid form, they may form crystals, e.g. in hydrated form.

Irrespective of the precise structure of the complex or complexes of the compositions described in Method 1.0, et seq, however, the interaction of the zinc and the amino acid converts insoluble zinc oxide or zinc salts to a highly soluble complex at approximately neutral pH. With increasing dilution in water, however, the complex disassociates, and the zinc ion converts to insoluble zinc oxide. This dynamic is unexpected—typically ionic compositions become more soluble at higher dilution, not less—and this facilitates deposition of the zinc precipitate on the teeth upon administration, in the presence of saliva and with rinsing. This precipitation occludes the dentinal tubules, thereby reducing hypersensitivity, and also provides zinc to the enamel, which reduces acid erosion, biofilm and plaque formation.

It will be understood that other amino acids can be used in place of lysine in the foregoing scheme. It will also be understood that, although the zinc, amino acid and optionally halide may be primarily in the form of precursor materials or in the form of an ionic complex, there may be some degree of equilibrium, so that the proportion of material which is actually in complex compared to the proportion in precursor form may vary depending on the precise conditions of formulation, concentration of materials, pH, presence or absence of water, presence or absence of other charged molecules, and so forth.

In a particular embodiment, the active is provided in a toothpaste. Upon brushing, the active is diluted by saliva and water, leading to precipitation and the formation of deposits and occluding particles.

DETAILED DESCRIPTION

As used herein, the term "oral composition" means the total composition that is delivered to the oral surfaces. The composition is further defined as a product which, during the normal course of usage, is not, the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively, the oral composition may be dual phase dispensed from a separated compartment dispenser.

"Dental Erosion" or "Erosion of tooth enamel", as used herein, is defined as an irreversible loss of dental hard tissue caused by a chemical process (i.e., exposure to intrinsic acid) that does not involve bacteria.

The word "effective amount" is intended to encompass a therapeutically effective amount to treat a specific disease or disorder or symptom.

The term "subject" includes human or non-human (i.e., animal) subjects or patients. In a particular embodiment, the invention encompasses both human and nonhuman subjects. In another embodiment, the invention encompasses nonhuman. In other embodiment, the term encompasses human.

The term "gastric acid" refers to gastric acid or stomach acid, wherein the gastric acid or stomach acid is a digestive fluid which is formed in the stomach, and is composed of hydrochloric acid, potassium chloride, and sodium chloride.

Unless otherwise specified, all percentages and amounts expressed herein and elsewhere in the specification should be understood to refer to percentages by weight. The amounts given are based on the active weight of the material.

Active Agents:

The compositions of the disclosure may comprise various agents which are active to protect and enhance the strength and integrity of the enamel and tooth structure and/or to reduce bacteria and associated tooth decay and/or gum disease, including or in addition to the zinc-amino acid complexes. Effective concentration of the active ingredients used herein will depend on the particular agent and the delivery system used. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product. Levels of antibacterial agents will vary similarly. For example, a triclosan toothpaste may contain about 0.3 wt % triclosan.

Fluoride Ion Source:

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the disclosure may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the disclosure at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counterion in the salt.

Abrasives:

The compositions of the disclosure, e.g. any of the compositions described in Method 1.0 et seq., include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Abrasives comprising insoluble or poorly soluble phosphate salts are not considered to fall within the "one or more soluble phosphate salts" referred to herein.

Other silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason. In certain embodiments, abrasive materials useful in the practice of the oral care compositions in accordance with the disclosure include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the disclosure are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present disclosure.

Foaming Agents:

The oral care compositions of the disclosure also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present disclosure. Polyoxyethylene is also commonly known as polyethylene glycol ("PEG") or polyethylene oxide. The polyoxyethylenes suitable for this disclosure will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present disclosure. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

Surfactants:

The compositions useful in the disclosure may contain anionic surfactants, for example:
  i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
  ii. higher alkyl sulfates, such as sodium lauryl sulfate,
  iii. higher alkyl-ether sulfates, e.g., of formula $CH_3(CH_2)_m CH_2(OCH_2CH_2)_nOSO_3X$, wherein m is 6-16, e.g., 10, n is 1-6, e.g., 2, 3 or 4, and X is Na or K, for example sodium laureth-2 sulfate ($CH_3(CH_2)_{10}CH_2(OCH_2CH_2)_2OSO_3Na$).
  iv. higher alkyl aryl sulfonates such as sodium dodecyl benzene sulfonate (sodium lauryl benzene sulfonate)
  v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the disclosure, e.g., any of the compositions described in Method 1.0 et seq., may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the disclosure, e.g., any of the compositions described in Method 1.0, et seq., comprises sodium lauryl sulfate.

The surfactant or mixtures of compatible surfactants can be present in the compositions of the present disclosure in about 0.1% to about 5.0%, in another embodiment about 0.3% to about 3.0% and in another embodiment about 0.5% to about 2.0% by weight of the total composition.

Tartar Control Agents:

In various embodiments of the present disclosure, the compositions, e.g., any of the compositions described in Method 1 et seq., comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The disclosure thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In one embodiment, tetrasodium pyrophosphate (TSPP), sodium tripolyphosphate (STPP), tetrapotassium pyrophosphate (TKPP), or mixtures thereof are used. In another embodiment, the compositions comprise a mixture of tetrasodium pyrophosphate (TSPP) and sodium tripolyphosphate (STPP)($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Flavoring Agents:

The oral care compositions, e.g., any of the compositions described in Method 1 et seq., of the disclosure may also include a flavoring agent. Flavoring agents which are used in the practice of the present disclosure include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight e.g. about 0.5 to about 1.5% by weight.

Polymers:

The oral care compositions of the disclosure may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water-soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water-soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of about 0.5% to about 5.0% by weight of the total composition are used.

The compositions of the disclosure, e.g., any of the compositions described in Method 1.0 et seq., may include an anionic polymer, for example in an amount of from about 0.05 to about 5%. Such agents are known generally for use in dentifrice, although not for this particular application, useful in the present disclosure are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

Water:

The oral compositions comprise water. Water employed in the preparation of commercial oral compositions should be deionized and free of organic impurities. The amount of water in the compositions includes the free water which is added plus that amount which is introduced with other materials. The oral composition, e.g., any of the compositions described in Method 1 et seq., may comprise water in the amount of 1-20% by weight, e.g. 5-18% by weight, e.g. 7-19% by weight, e.g. 8-17% by weight, e.g., 9-16% by weight, about 10% by weight, and all ranges and sub ranges there between.

Humectants:

Within certain embodiments of the oral compositions, e.g., any of the compositions described in Method 1.0 et seq., it is also desirable to incorporate a humectant to prevent the composition from hardening upon exposure to air. Certain humectants can also impart desirable sweetness or flavor to dentifrice compositions. Suitable humectants include edible polyhydric alcohols such as glycerin, sorbitol, xylitol, propylene glycol as well as other polyols and mixtures of these humectants. In one embodiment of the disclosure, the principal humectant is glycerin, which may be present at levels of greater than 25%, e.g. 25-35% about 30%, with 5% or less of other humectants.

Other Optional Ingredients:

In addition to the above-described components, the embodiments of this disclosure can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Unless stated otherwise, all percentages of composition components given in this specification are by weight based on a total composition or formulation weight of 100%.

Unless otherwise specifically identified, the ingredients for use in the compositions and formulations of the present disclosure are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this disclosure, and includes for example excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the disclosure extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The present invention in its method aspect involves applying to the oral cavity a safe and effective amount of the compositions described herein.

The compositions and methods according to the invention (e.g., compositions described in Method 1.0, et seq) can be incorporated into oral compositions for the care of the mouth and teeth such as toothpastes, transparent pastes, gels, mouth rinses, sprays and chewing gum.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

Preparation of Demineralization and Treatment Solutions

An aqueous 1% (w/w) citric acid stock solution is prepared by dissolving anhydrous citric acid powder in deionized water with stirring at room temperature. The acidity is adjusted to pH 3.8 with 1M NaOH Additional deionized water is added to a total mass of 1000 g (pH 3.77). Dentifrice slurries (1:2) are generated by suspending the indicated dentifrice and deionized water followed by speed mixing for 2 minutes. Three separate slurries are generated for each toothpaste to permit three separate replicates for each toothpaste dose tested.

Demineralization Procedure

Toothpaste slurry (at the indicated amounts, Table 1) was added to 0.2 g of calcium deficient carbonated hydroxyapatite (HA) powder (Himed) massed into a 14 mL culture tube. Calcium-deficient HA powder is chosen as the mimic calcium-phosphate material given its similarity in structure and elemental composition to dental enamel, Citric acid (as indicated) is immediately added sequentially. The resultants suspensions are mixed on an orbital shaker for 1 hour. Samples are then centrifuged at 4000 rpm for 5 minutes to pellet the HA powder. The pH of the supernatant is obtained and a portion of the supernatant (1 mL) is removed for elemental analysis. To prepare the samples for analytical analysis, the supernatant aliquot (1 mL) is combined with concentrated nitric acid (1 mL) for 10 minutes. The whole solution is then diluted to a total volume of 10 mL with DI water. Samples are ether filtered or centrifuged to remove residual insoluble material.

TABLE 1

Experimental setup depicting ratios of demineralization solution and toothpaste slurry for incubation with HA powder.

| Dilution Factor of 1:2 Slurry | Toothpaste Slurry (1:2), µL | Demineralization Solution (µL) |
|---|---|---|
| 4 | 5000 | 5000 |
| 8 | 2500 | 7500 |
| 20 | 1000 | 9000 |
| 40 | 500 | 9500 |
| 80 | 250 | 9750 |

Method Validation:

To validate the method, the effect on calcium release for a no fluoride dentifrice ("Negative Control") is compared to a commercially available dentifrice. Here, the commercially-available dentifrice ("Positive control") contains 0.3% triclosan, 2% PVM/MA copolymer, and 1450 ppm F as sodium fluoride in a silica base. The Positive Control does not contain zinc. As a function of toothpaste dilution factor, the fluoride effect in prevention of calcium release is clear from Table 2. The no fluoride toothpaste shows no dose response while the fluoride toothpaste showed characteristic calcium release dependent upon the toothpaste dilution factor.

TABLE 2

| Toothpaste Dilution Factor | Negative Control (Calcium Released (ppm)) | Positive Control Calcium Released (ppm) |
|---|---|---|
| 4 | 1014 ± 82 | 94 ± 15 |
| 8 | 1165 ± 77 | 126 ± 4 |
| 20 | 1125 ± 146 | 198 ± 11 |
| 40 | 1151 ± 118 | 247 ± 13 |
| 80 | 991 ± 76 | 331 ± 53 |

Example 2

The present example illustrates that zinc toothpaste inhibits calcium release beyond any fluoride effects. Discernible differences are observed in the amount of calcium released between:

a.) Toothpaste slurries of the Test Formulation containing 1.05% zinc oxide, 4.75% L-lysine.HCl, and 1450 ppm sodium fluoride in a silica base; and b.) Toothpaste slurries of the Positive Control (i.e., the commercial product) containing 0.3% triclosan, 2% PVM/MA copolymer, and 1450 ppm F as sodium fluoride in a silica base.

Here, prevention of calcium release was statistically decreased over all ranges of toothpaste slurries (regardless of dilution factor) in the Test Formulation as compared to the Positive Control. Fluoride levels are equal in both the Test Formulation and Positive Control. Therefore, this data suggests that the active materials in the zinc formulas (i.e., Test Formulation) are having an effect on the amount of calcium released.

TABLE 3

| Toothpaste Dilution Factor | Positive Control (Calcium Released (ppm)) | Test Formulation Calcium Released (ppm) |
|---|---|---|
| 4 | 94 ± 15 | 37 ± 5 |
| 8 | 126 ± 4 | 50 ± 8 |
| 20 | 198 ± 11 | 103 ± 8 |
| 40 | 247 ± 13 | 139 ± 3 |
| 80 | 331 ± 53 | 186 ± 3 |

Example 3

The amount of zinc remaining in the solution is further measured by ICP analysis. A direct logarithmic correlation is observed between the calcium released and the concentration of zinc in the demineralization solution. Even at the lowest level of zinc (55 ppm) only approximately 186 ppm calcium is released with Test Formulations, to about a 44% improvement over the Positive control. Results are seen in Tables 5 and 6.

TABLE 5

Positive Control

| Toothpaste Dilution Factor | Zinc (ppm) | Calcium Released (ppm) |
|---|---|---|
| 4 | 0 | 94 ± 15 |
| 8 | 0 | 126 ± 4 |
| 20 | 0 | 198 ± 11 |
| 40 | 0 | 247 ± 13 |
| 80 | 0 | 331 ± 53 |

TABLE 6

Test Formulation

| Toothpaste Dilution Factor | Zinc (ppm) | Calcium Released (ppm) |
|---|---|---|
| 4 | 1244 ± 6 | 37 ± 5 |
| 8 | 581 ± 11 | 50 ± 8 |
| 20 | 255 ± 15 | 103 ± 8 |
| 40 | 115 ± 10 | 139 ± 3 |
| 80 | 46 ± 3 | 186 ± 3 |

Example 4—Representative Dentifrice Formulation

Representative Dentifrice Formulation:

| Ingredient | Formula 1 (by wt %) |
|---|---|
| DEMINERALIZED WATER | Q.S. |
| ABRASIVES | 15%-25% |

-continued

| Ingredient | Formula 1 (by wt %) |
|---|---|
| 99.0%-101.0% GLYCERIN - USP, EP VEG | 34%-37% |
| L-LYSINE MONOHYDROCHLORIDE | 0.5% |
| AMPHOTERIC SURFACTANT | 0.75%-1.25% |
| POLYMERS | 0.75%-1.5% |
| PHOSPHATE SALT | 1%-3% |
| SODIUM HYDROXIDE - 50% SOLUTION | 0.25%-0.75% |
| WHITENING AGENT | 0.5%-1.5% |
| FLAVORING AGENTS | 1.4%-1.9% |
| 35% HYDROCHLORIC ACID | 0-0.1% |
| SODIUM FLUORIDE - USP, EP | 0.32 |
| SILICA - THICKENER | 5%-7% |
| ANIONIC SURFACTANT | 1%-3% |
| ZINC OXIDE | 0.75%-1.25% |
| HUMECTANT | 6%-9% |
| Total Components | 100 |

Example 5—Representative Control Formulation

The following is a representative negative control dentifrice formulation for use in the above described examples, wherein the negative control formulation does not contain fluoride:

| Ingredient | Formula 1 (by wt. %) |
|---|---|
| DEMINERALIZED WATER | Q.S. |
| ABRASIVES | 7%-9% |
| Sorbitol - Non Crystal - 70% Solution | 65%-70% |
| AMPHOTERIC SURFACTANT | 1.0%-1.5% |
| NON-IONIC SURFACTANT | 0.25%-0.75% |
| POLYMERS | 0.75%-1.5% |
| WHITENING AGENT | 0.25%-1.0% |
| FLAVORING AGENTS | 1.0%-1.5% |
| 85% SYRUPY PHOSPHORIC ACID - FOOD GRADE | 0-0.35 |
| SILICA - THICKENER | 6%-9% |
| ANIONIC SURFACTANT | 1%-3% |
| Total Components | 100 |

While particular embodiments of the invention have been illustrated and described, it will be obvious to those skilled in the art that various changes and modifications may be made without departing from the scope of the invention as defined in the appended claims.

What is claimed is:

1. A method of treating one or more symptoms of a gastric disorder in the oral cavity of a subject in need thereof, wherein the method comprises applying to the subject's teeth an oral care composition comprising:
   a. a zinc-lysine-chloride complex (ZLC) in an amount of 2-6% by weight of the composition; and
   b. an orally acceptable carrier;
   wherein the gastric disorder is gastroesophageal reflux disease (GERD); and
   wherein the one or more symptoms of a gastric disorder comprise dental erosion due to loss of calcium in the subject's tooth enamel consequent to the presence of gastric acid in the oral cavity.

2. The method according to claim 1, wherein the oral care composition inhibits or decreases the release of calcium from the subject's tooth enamel.

3. The method according to claim 2, wherein the inhibition or decrease of the release of calcium in the subject's tooth enamel is relative to a reference standard.

4. The method according to claim 3, wherein the oral care composition inhibits the release of calcium relative to one or more compositions that do not contain zinc.

5. The method according to claim 1, wherein the one or more symptoms is that the subject is exposed to gastric acids in the oral cavity during sleep.

6. The method according to claim 1, wherein the subject is at risk for dental erosion.

7. The method according to claim 6, wherein the risk for dental erosion is selected from the group consisting of: xerostomia, tooth hypersensitivity, weakened tooth integrity, and tooth discoloration.

8. The method according to claim 1, wherein the oral care composition comprises:
   a. the zinc-amino acid complex is ZLC in an amount of 2-6% by weight of the composition;
   b. one or more soluble phosphate salts are selected from tetrasodium pyrophosphate (TSPP), sodium tripolyphosphate (STPP), tetrapotassium pyrophosphate (TKPP), and
   c. combinations thereof in an amount of 2-6% by weight of the composition; and
   d. the a dentifrice base comprising comprises an effective amount of a fluoride ion source,
   silicas,
   humectant,
   thickener,
   anionic surfactant,
   zwitterionic surfactant,
   flavoring and sweetener.

* * * * *